United States Patent

Shah et al.

(10) Patent No.: US 9,116,201 B2
(45) Date of Patent: Aug. 25, 2015

(54) METHOD FOR DETECTING ZERO-FIELD RESONANCE

(71) Applicants: Vishal Shah, Westminster, CO (US); Kenneth Jeramiah Hughes, Lafayette, CO (US)

(72) Inventors: Vishal Shah, Westminster, CO (US); Kenneth Jeramiah Hughes, Lafayette, CO (US)

(73) Assignee: QuSpin Inc., Louisville, CO (US)

( * ) Notice: Subject to any disclaimer, the term of this patent is extended or adjusted under 35 U.S.C. 154(b) by 0 days.

(21) Appl. No.: 14/611,135

(22) Filed: Jan. 30, 2015

(65) Prior Publication Data

US 2015/0212168 A1 Jul. 30, 2015

Related U.S. Application Data

(60) Provisional application No. 61/965,455, filed on Jan. 30, 2014.

(51) Int. Cl.
*G01V 3/00* (2006.01)
*G01R 33/26* (2006.01)
*G01N 24/00* (2006.01)

(52) U.S. Cl.
CPC ............ *G01R 33/26* (2013.01); *G01N 24/006* (2013.01)

(58) Field of Classification Search
CPC ..................................... G01R 33/26
USPC .......................... 324/304, 301, 300
See application file for complete search history.

(56) References Cited

U.S. PATENT DOCUMENTS

| | | | |
|---|---|---|---|
| 3,629,697 A | 12/1971 | Bouchiat et al. | |
| 3,786,340 A | 1/1974 | Otten et al. | |
| 4,005,355 A | 1/1977 | Happer et al. | |
| 7,145,333 B2 | 12/2006 | Romalis et al. | |
| 8,212,556 B1 | 7/2012 | Schwindt et al. | |
| 8,917,091 B2 * | 12/2014 | Le Prado et al. | 324/244 |
| 2010/0188081 A1 * | 7/2010 | Lammegger | 324/304 |
| 2015/0008916 A1 * | 1/2015 | Le Prado et al. | 324/304 |

OTHER PUBLICATIONS

Budker, D., & Romalis, M. (2007). Optical magnetometry. Nat Phys, 3(4), 227-234. doi:10.1038/nphys566.

Dong, H. f., Fang, J. c., Zhou, B. q., Tang X. b., & Qin, J. (2012). Three-dimensional atomic magnetometry. The European Physical Journal—Applied Physics, 57(02), null-null. doi:10.1051/epjap/2011110392.

Dupont-Roc, J., Haroche, S., & Cohen-Tannoudji, C. (1969). Detection of very weak magnetic fields (10-9gauss) by 87Rb zero-field level crossing resonances. Physics Letters A, 28(9), 638-639. doi:10.1016/0375-9601(69)90480-0.

(Continued)

*Primary Examiner* — Louis Arana
(74) *Attorney, Agent, or Firm* — Superior Patent Group; Patricia C. Brzostowicz

(57) ABSTRACT

A zero-field paramagnetic resonance magnetometer (ZF-PRM) system and method for quickly and efficiently finding and optimizing the zero-field (ZF) resonance is described. In this system and method a magnetic coil is used to apply a magnetic bias field in the direction of the pump beam to artificially broaden the width and maximize the strength of the ZF resonance. By making the ZF resonance easy to detect, the ZF resonance may be found quickly found without the use of additional components and complex algorithms. Once the ZF resonance is found, a compensating magnetic field can be applied to null the magnetic field in the vicinity of the vapor cell in the ZF-PRM, thereby initializing it for operation.

24 Claims, 9 Drawing Sheets

(56) References Cited

OTHER PUBLICATIONS

Happer, W., & Mathur, B. S. (1967). Effective Operator Formalism in Optical Pumping. Physical Review, 163(1), 12. doi:10.1103/PhysRev.163.12.

Seltzer, S. J., & Romalis, M. V. (2004). Unshielded three-axis vector operation of a spin-exchange-relaxation-free atomic magnetometer. Applied Physics Letters, 85(20), 4804-4806. doi:doi:10.1063/1.1814434.

Shah, V., Knappe, S., Schwindt P. D. D., & Kitching J. (2007). Subpicotesla atomic magnetometry with a microfabricated vapour cell. Nat Photon, 1(11), 649-652. doi:10.1038/nphoton.2007.201.

Slocum, R. E., & Reilly, F. N. (1963). Low Field Helium Magnetometer for Space Applications. IEEE Transactions on Nuclear Science, 10(1), 165-171. doi:10.1109/TNS.1963.4323257.

Weinstock, H. (1996). Squid Sensors: Fundamentals, Fabrication and Applications (NATO Science Series E: (1st ed.). Springer.

Vishal K. Shah and Ronald T. Wakai;A Compact, High Performance Atomic Magnetometer for Biomedical Applications;Phys Med Biol. Nov. 21, 2013; 58(22): 8153-8161. doi:10.1088/0031-9155/58/22/8153.

Seltzer, S. (2008). Developments in Alkali-Metal Atomic Magnetometry (PhD Dissertation). Princeton University.

Fang, J., & Qin, J. (2012). In situ triaxial magnetic field compensation for the spin-exchange-relaxation-free atomic magnetometer. The Review of Scientific Instruments, 83(10), 103104. doi:10.1063/1.4756046.

* cited by examiner

METHOD FOR DETECTING ZERO-FIELD RESONANCE

REFERENCE TO RELATED APPLICATIONS

This application claims priority to U.S. Provisional Application No. 61/965,455 filed Jan. 30, 2014.

FIELD OF INVENTION

This disclosure relates to the field of paramagnetic resonance magnetometers and in particular a magnetometer and an accompanying method for detecting background magnetic fields. Further, the disclosure relates to a method for compensating for the background magnetic field and measuring a target magnetic field.

BACKGROUND

High sensitivity magnetometers, including paramagnetic resonance magnetometers (PRM) (Slocum & Reilly, 1963), have a wide range of applications including, but not limited to the following: fundamental research, detecting biomagnetic signals (such as those emanating from biological organisms, including the human body), geophysical exploration and prospecting, navigation and space applications, and military uses (such as ordinance and underground-underwater structure detection). Until recently, the most sensitive and commercially available magnetometers for such applications were based on superconducting quantum interference devices (SQUID) (Weinstock, 1996). However, zero-field paramagnetic resonance magnetometers (ZF-PRM); (Dupont-Roc, Haroche, & Cohen-Tannoudji, 1969; Marie-Anne et al., 1971; Shah, Knappe, Schwindt, & Kitching, 2007; W & E, 1974), which have advanced to comparable sensitivity as SQUID systems, have recently gained popularity as a lower-cost, more robust alternative to SQUID magnetometers for many applications. The current rapid development and commercialization of such atomic based magnetic sensors may lead to replacement of SQUID based sensors for many existing applications primarily because ZF-PRMs do not require cryogenic cooling.

Significant developments in alkali atomic magnetometery (Budker & Romalis, 2007) over the past decade have led to a variety of techniques and methods for sensing magnetic fields. In general, the different methods are based on the same fundamental physical sensing mechanism that exploits the energy structure of atoms and the perturbations that result in their energy levels (or spin state) from exposure to external magnetic fields. In essence, atomic based magnetic sensors measure the direction and magnitude of an external magnetic field through the induced changes in the atomic spin polarization of an ensemble of atoms.

A ZF-PRM relies on detecting changes in optical transmission properties of atomic vapor around a narrow ZF atomic resonance to measure the magnitude and direction of the background magnetic field. Generally a ZF resonance can only be observed when the atomic vapor (the ensemble of atoms) in the magnetometer is subjected to very small magnetic fields, generally less than 100 nanotesla (nT). Typically, the full width of the ZF resonance is less than 30 nT. It is therefore necessary for the ambient magnetic field at the location of ZF-PRM to be less than the detection range of the magnetometer. The detection range of a ZF-PRM is typically a fraction (less than about 1, for example, one half) of the width of the ZF resonance. The magnetometer becomes less sensitive or even insensitive when the total background magnetic field is greater than the detection range. For this reason, the ZF-PRMs are frequently used inside magnetically shielded environments in which the ambient magnetic field is very small, typically few tens of nT or less. When ZF-PRM is used in an unshielded or poorly shielded environment where a large background magnetic field is present, external biasing coils are used to null the magnetic field in vicinity of the ZF-PRM, keeping the magnetometer within its detection range. This operational requirement of near ZF condition limits the utility of ZF-PRMs for many applications; this includes biomedical applications, such as Magnetoencephalography (MEG) and Magnetocardiography (MCG) where large and expensive shielded volumes are required, as well as any outdoor applications where magnetic shielding is impractical.

SUMMARY OF THE INVENTION

This invention relates to the use of a ZF-PRM in any magnetic field environment, including in unshielded magnetic field environments, using an apparatus and accompanying methods provided herein to actively null the background or ambient magnetic fields. The act of nulling a field, wherein the field is effectively equal to zero, can occur when the width of the measured resonance is minimized and height is maximized, and is therefore said to be optimized. This nulling may be generated using a set of external coils (to compensate in all three axes) that produce the desired opposing magnetic fields. Precisely zeroing the magnetic field is a complex and cumbersome task and often requires precise a priori knowledge of the ambient field. The apparatus and method presented here offers a solution to zeroing the field without a priori knowledge of the ambient field with the additional benefit of lower cost and time expenditures compared to other methods.

We note that the present apparatus and method solves a long-standing complexity which has been recognized by those skilled in the art of building and operating ZF-PRMs. To highlight the importance of our method, we include here text from recent prior art by leaders in field of ZF-PRM who are skilled in the art:

"We find that the easiest method for zeroing the magnetic field is to use a different sensor, such as a fluxgate, and then turn on feedback from the magnetometer once the field along all three directions is sufficiently small. Zeroing the field using only the magnetometer signal is extremely difficult and inefficient, especially when the field amplitude is much larger than the magnetic linewidth. Once feedback is active, the magnetometer is able to track changes in the local environment, such as motion of distant magnetic objects." (S. Seltzer, 2008, "Developments in Alkali-Metal Atomic Magnetometry", PhD Dissertation, Ch. 5, Pg. 156)

"Because the earth field amplitude is much larger than the dynamic range of atomic vector magnetometer, zeroing the field using only atomic signal is extremely difficult and inefficient." (Haifeng Dong, Lin, & Tang, 2013, "Atomic-Signal-Based Zero-Field Finding Technique for Unshielded Atomic Vector Magnetometer", IEEE Sensors Journal, 13(1), 186-189)

"With the magnetic field unknown, it is difficult to tell whether the condition has been satisfied or not, so it is not convenient to use this method for triaxial magnetic field compensation. This is why fluxgate magnetometers are usually used to measure the triaxial magnetic fields to guarantee operation of the SERF atomic magnetometer under magnetic shield room conditions." (Fang & Qin, 2012, "In situ triaxial magnetic field compensation for the spin-exchange-relaxation-free atomic magnetometer", *The Review of Scientific Instruments,* 83(10), 103104)

In general, the natural ZF resonance is not only very narrow, but occurs when the magnitude of the magnetic field is very close to zero. Because the earth's magnetic field [~50 microtesla (μT)] is many orders of magnitude larger than the width of the natural ZF resonance (~30 nT or less), locating the natural ZF resonance by simply scanning the nulling field in all three directions without prior knowledge of the magnitude and direction of the background field is akin to finding a needle in a haystack.

To scan through all possible field values in steps of 15 nT increments, i.e. to insure the detection of the resonance signal, in each of the three axial directions would require (50 μT/15 nT)^3 or 37,037,037,037, roughly 37 trillion steps. It is thus a very time intensive task to find the ZF resonance condition in an unknown magnetic field environment without the use of external aids to provide some information about the magnitude and direction of the ambient magnetic field.

Algorithms and techniques have been developed to scan for the ZF resonance more effectively. Such methods are considerably complex, time consuming, and impractical for many applications.

As eluded to above, a prior art method uses a separate high-performance triaxial fluxgate magnetometer to accurately measure the magnitude and direction of the background magnetic field and then apply compensating fields to null the total ambient magnetic field at the location of the fluxgate (S. Seltzer, 2008; S. J. Seltzer & Romalis, 2004). After approximately zeroing the field, the fluxgate magnetometer is removed and replaced by ZF-PRM. This method significantly reduces the scan range and time necessary to find the ZF resonance. However, this method also adds additional equipment and complexity, and therefor expense, to the system. The ZF-PRM as well as a fluxgate magnetometer may cost at least several thousand dollars each, such that addition of the fluxgate magnetometer may more than double the cost of the system. In addition, the fluxgate magnetometers often have intrinsic magnetism, which is why they have to be physically removed and placed away from ZF-PRM when the ZF-PRM is in operation.

Another technique for nulling the background field using ZF-PRM alone was developed by (Haifeng Dong et al., 2013), who used an iterative convergence algorithm based on an approximate prior knowledge of the magnitude and direction of earth's magnetic field. Fang & Qin, 2012, have used another iterative convergence algorithm that works under favorable initial conditions such that the transverse field components (Bx and By) are not much greater than the longitudinal field component (Bz). As is illustrated in FIG. 1, Bx and By is the magnitude of the magnetic field components in a direction perpendicular to a pump beam 20, as is described in more detail in the discussion of FIG. 1, following, and Bz is the magnetic field parallel to the pump beam 20.

What is needed in the art is a simple, quick, and inexpensive method of finding and nulling the ambient magnetic field such that small field changes may be measured in any environment. The present invention solves this problem, being a system and method that provides such a simple, inexpensive, and fast method for zeroing the magnetic field without a priori knowledge of the background field.

This example system and method is a novel system and method for finding paramagnetic resonance in an unknown magnetic field. Summarizing the operation of a ZF-PRM 101, illustrated by FIG. 1, the behavior of the spin polarization vector ($\vec{P}$) of alkali atoms 60 in a sensing cell 70 can be understood based on the Bloch equation:

$$\frac{d\vec{P}}{dt} = \gamma(\vec{B} \times \vec{P}) - R(\vec{P} - \vec{P}_0), \quad \text{(Eq. 1)}$$

where γ is the gyromagnetic ratio of the alkali atoms 60, R is the combined optical pumping and relaxation rate, $\vec{P}_0$ is the equilibrium spin polarization of alkali atoms 60, and $\vec{B}$ is the magnetic field to which alkali atoms are exposed. A representation of a magnetic field may be detected as a change in transmission of the light or pump light beam through the alkali atoms by a photodetector. The amount of light beam 20 transmitted is proportional to the steady state solution of the said equations along the z-direction, i.e.:

$$P_z = P_0 \frac{B_z^2 + \left(\frac{R}{\gamma}\right)^2}{B_x^2 + B_y^2 + B_z^2 + \left(\frac{R}{\gamma}\right)^2}, \quad \text{(Eq. 2)}$$

where $P_z$ is the component of the spin polarization vector, $\vec{P}$, in the z-direction.

When By (or Bx) and Bz is near zero, a change in the amount of light transmitted through the vapor cell can be observed when the Bx (or By) field is scanned about the ZF value. This change in transmission properties of the vapor cell is referred to as ZF resonance and its width is equal to $$\left(\frac{R}{\gamma}\right),$$

which is on the order of about 30 nT or less. As illustrated in FIG. 2, ZF resonance R is expressed as a signal having height, H, and width, W. The derivative of the resonance produces a dispersion curve which we refer to herein as the error signal E. The derivative peak E is used to lock the field values as will be described later. ZF-PRM with different configurations, such as those illustrated in FIG. 3 and FIG. 4, may have different shaped resonance curves, which may look for example like signal E, or another shape, which will still have a height and width value, the height and width being measured from peak to peak.

When By and Bz fields are non-zero, the width of the resonance, W, in the x-direction is given by:

$$W = \sqrt{B_y^2 + B_z^2 + \left(\frac{R}{\gamma}\right)^2} \quad \text{(Eq. 3)}$$

and the height, H, of the ZF resonance is proportional to, $P_z$, and is given by:

$$H \propto P_z = P_0 \frac{B_z^2 + \left(\frac{R}{\gamma}\right)^2}{B_y^2 + B_z^2 + \left(\frac{R}{\gamma}\right)^2} \quad \text{(Eq. 4)}$$

From Eq. 4, we see that when By is significantly greater than Bz, the amplitude of the resonance is significantly diminished and may not be observable by simply scanning the magnetic field in x-direction alone. Consequently, attempting to find the ZF resonance without prior knowledge of the magnitude and direction of the background field can be a cumbersome task.

In the example system and method of the present invention, a strong magnetic field, or bias field, $Bz^t$, is applied to the vapor cell along the direction of the light beam used to pump atoms in the vapor cell. As an example, the value of the bias field, may be less than the value of the background magnetic field in which the ZF-PRM is designed to operate, or preferably at least as great as the value of the background field in which the ZF-PRM is designed to operate, or at least greater than the value of the background field in which the ZF-PRM is designed to operate, or even as much as at least twice the maximum value of the background field in which the ZF-PRM is designed to operate, or more. Applying a strong bias field $Bz^t$ ensures that the condition By>>Bz or Bx>>Bz is never met regardless of the orientation of the magnetometer with respect to the ambient field, and therefore, the amplitude of a resonance peak will not be diminished by the presence of any transverse field. Additionally, the width of the resonance peak greatly increases from applying a bias field, $Bz^t$, as seen from Eq. 2. To summarize, the method of applying a bias field, $Bz^t$, presented herein, ensures that the ZF resonance is both wide and strong in amplitude, or height, such that locating the ZF resonance is straightforward, fast, and requires no additional equipment, or complex algorithms.

Once the ZF resonance is detected, compensating fields can be applied in a way that results in a ZF resonance with minimum width and maximum amplitude, i.e. height. For ZF resonance in x-direction, the value of the compensating magnetic field that produces minimum width and maximum amplitude is the point at which the magnetic field is closest to zero at the location of the vapor cell in y-direction and z-direction. The compensating magnetic field value corresponding to the peak of the resonance gives magnetic field closest to zero at the location of the vapor cell in the x-direction. The ZF-PRM is maximally sensitive when magnetic field is nearly zero in all three directions at the location of the vapor cell.

As such an example method for identifying and optimizing a ZF resonance using a paramagnetic resonance magnetometer, is described and claimed herein. The example method comprises the steps of: directing at least one pump light beam through a vapor cell containing gaseous atoms to increase the magnetic polarization of the gaseous atoms; measuring light transmitted through the vapor cell; in a non-iterative action, applying a strong magnetic field having a direction along the pump light beam to simultaneously increase the height and width of the ZF resonance, and subsequently detecting the ZF resonance; scanning a magnetic field in a direction differing from that of the pump light beam; and adjusting magnetic field components generated by one or more coils to minimize the width and maximize the height of the zero-field resonance.

The strong magnetic field applied along the direction of the pump light beam may be at least about as strong as a background magnetic field, or even stronger than the background magnetic field. Alternately, the strong magnetic field applied along the direction of the pump light beam may be weaker than the background magnetic field.

The gaseous atoms in the vapor cell may be selected from a group consisting of rubidium, cesium, potassium, sodium, and helium. Further, the magnetometer may be oriented along any arbitrary direction with respect to a background magnetic field. Additionally, the magnetometer need not be placed within a magnetic shield.

The scanning of the magnetic field in a direction differing from that of the pump light beam, occurs within a range, the scan range may be at least about 0.1 times as strong, or at least about 0.5 times as strong, or at least about as strong as the magnetic field in the direction of the pump light beam. Further, the scan range may be as much as 2 times, or even as much as 5 times, or even as much as 10 times as strong as the magnetic field in the direction of the pump light beam.

The example method, further enhanced for precision offset field generation, may further comprise the step of adding a calibrated field. The calibrated field may be generated by one or more coils that may be internal or external to the magnetometer. Further, the one or more coils may be an additional single coil, or an additional two coils, or set of coils, or the sole coil, or coils, or set of coils of the magnetometer.

A second example for locking a zero-field paramagnetic resonance magnetometer (ZF-PRM) to a ZF resonance is presented and claimed herein. This second example method comprises steps of directing at least one pump light beam through a vapor cell containing gaseous atoms to increase the magnetic polarization of the gaseous atoms; measuring light transmitted through the vapor cell; in a non-iterative action, applying a strong magnetic field having a direction along the pump light beam to simultaneously increase the height and width of the ZF resonance; applying a modulation current having an amplitude to at least one coil transverse to the pump light beam; generating at least one error signal; and subsequent to applying the strong magnetic field having a direction along the pump light beam, engaging at least one control loop to minimize at least one field component that is transverse to the pump light beam.

The strong magnetic field applied along the direction of the pump light beam is at least about as strong as a background magnetic field, or even stronger than the background magnetic field. Alternately, the strong magnetic field applied along the direction of the pump light beam may be weaker than the background magnetic field.

The gaseous atoms in the vapor cell may be selected from a group consisting of rubidium, cesium, potassium, sodium, and helium. Further, the magnetometer may be oriented along any arbitrary direction with respect to a background magnetic field. Additionally, the magnetometer need not placed within a magnetic shield.

Further, the modulation current may be applied to at least two coils transverse to the pump light beam, such that at least two error signals are generated. The modulation current may be applied to at least three coils transverse to the pump light beam, such that at least three error signals are generated.

This example method for locking a ZF-PRM to a ZF resonance may further comprise the steps of changing the amplitude of at least one modulation current and optimizing at least one error signal.

Inasmuch, this example method for locking a ZF-PRM to a ZF resonance, may yet further comprise the step of engaging at least one control loop that minimizes the field component in the direction along the pump beam, this step being subsequent to the step of engaging at least one control loop to minimize at least one field component that is transverse to the pump light beam.

The method may be further enhanced for precision offset field generation and further comprise deactivating one or more control loops, and subsequently adding a calibrated field. The calibrated field may be generated by one or more coils that are either internal or external to the magnetometer. Further, the one or more coils may be an additional single coil, or an additional two coils, or set of coils, or the sole coil, or coils, or set of coils of the magnetometer. Even so, the method may further comprise adding one or more calibrated offsets to one or more control loops.

For the purposes of the present application the term "field" when not accompanied by a qualifier is defined to mean magnetic field. The terms "large" or "strong" when referring to a field are defined as a field with a magnitude having a range at least about 0.1 times the background field to as much as about 10 times the background field. The terms "background" and "ambient" when qualifying a field are interchangeable. The term "background magnetic field", or equivalently "background field" is defined to mean a field to which the magnetometer is subjected, but which was not applied by the user or the magnetometer operation. As one example, Earth's magnetic field would be considered part of the background field for a magnetometer placed outside. Other parts of the background field could include nearby magnetic objects like cars or buildings. The term "bias field" is defined to be a magnetic field that is applied by the user, typically with a coil, for the operation of the magnetometer. A field has both direction and magnitude and herein the term "field component" refers to the field along a given direction.

Further, the term "coil" is known in the art and defined to be an object that can produce a tunable magnetic field. One example of a coil is a wire that has been wound in a circular shape through which electrical current is passed to produce a magnetic field. Other geometries of a coil could include, but are not limited to a Helmholtz coil pair, a round solenoid, or a wire wrapped in rectangular-shaped windings. Herein the term "null" means to apply a field to cancel a component of the background field. As one example of the term "null", an x-bias coil is positioned with the axis of the coil along the x-direction. Continuing the example, current is applied to the coil to generate a field, at a desired point, that is equal in magnitude and opposite in direction to the background field at that point. Further continuing the example, the sum of the x-component of the background field with the x-component of the applied bias field is zero, thus the x component of the field has been nulled.

Herein the term "modulation" is used to describe periodic variations in either a field or an electrical current that drives a coil. Similarly, the term "modulate" is defined herein to be the act of apply such modulation. Specifically the terms "modulate" and "modulation" apply to periodic variations that enable error signal generation, as one example, through the lock-in detection technique. The term lock-in detection is known in the art. The term "scan" or "scanning" is used in conjunction with a parameter and is defined herein to mean the act of changing a parameter to make a manual (visual) or computer-aided observation. As an example, one may scan the field to observe the shape of the zero-field resonance using an oscilloscope. The "scan" need not be periodic as is required with "modulation". The term "optimizing a zero-field resonance" is used herein in to describe the minimizing the width and maximizing the height of the ZF resonance. Further, the act of nulling a field, wherein in the field is effectively equal to zero, can occur when the width of the measured resonance is minimized and height is maximized, and is therefore said to be optimized.

DETAILED DESCRIPTION OF THE INVENTION

Figure 1:
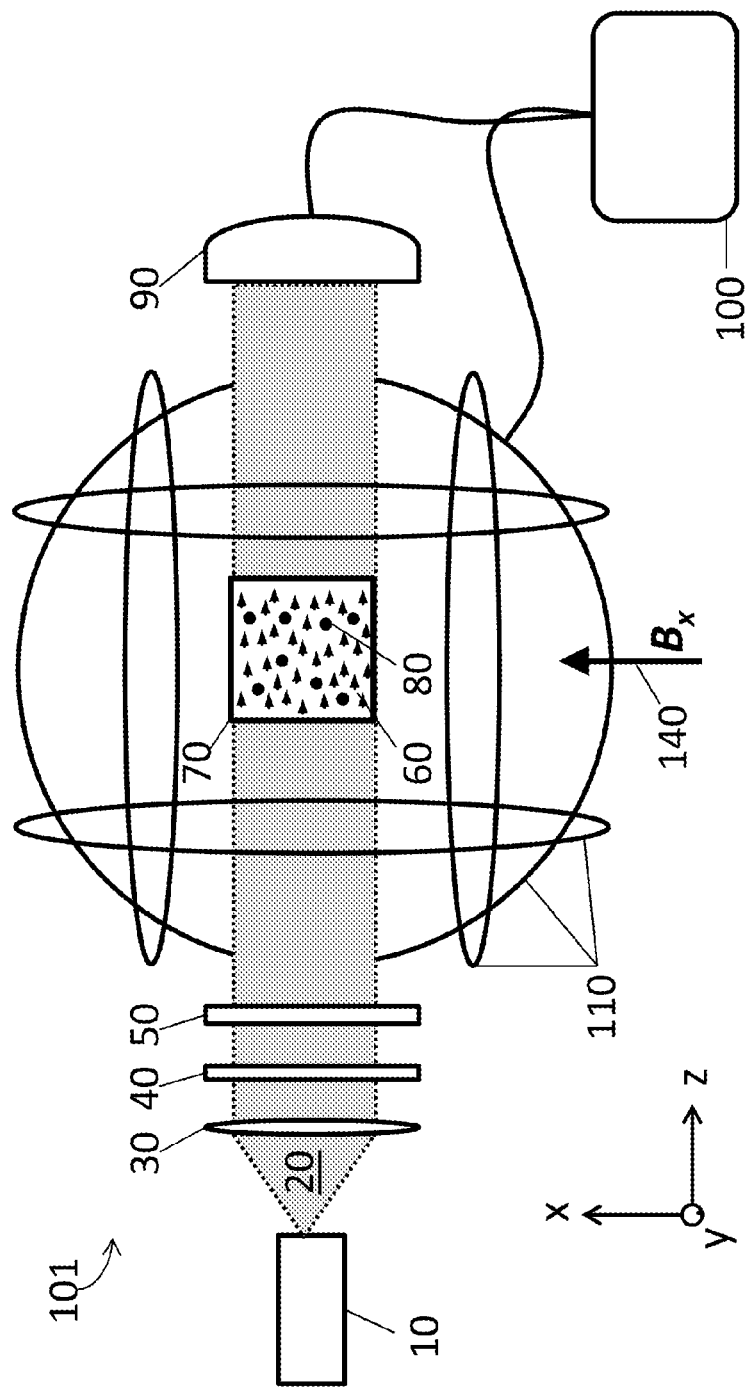
FIG. 1 schematically illustrates a prior art ZF-PRM system using a single light beam.

Paramagnetic resonance magnetometers as shown in FIG. 1, are known in the art as described previously as in U.S. Pat. No. 3,629,697 to Bouchiat et al., and U.S. Pat. No. 4,005,355 to Happer et al., both incorporated in full herein by reference. More recently, U.S. Pat. No. 8,212,556 to Schwindt et al., and U.S. Pat. No. 7,145,333 to Romalis et al. described a paramagnetic resonance magnetometer wherein two beams are used, one pump beam and a second probing beam, being illustrated in FIGS. 3 and 4 respectively, and incorporated in full herein by reference.

Figure 3:
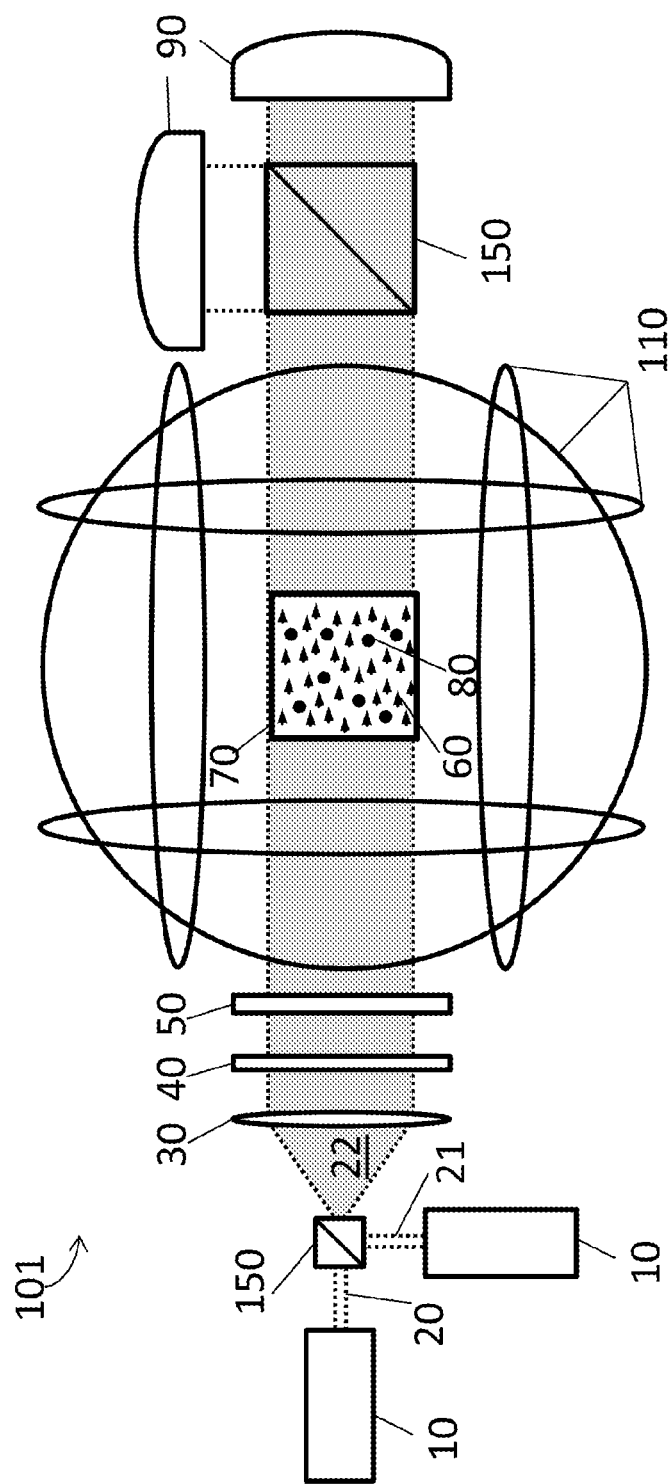
FIG. 3 schematically illustrates a prior art, parallel, dual light beam ZF-PRM system.
Figure 4:
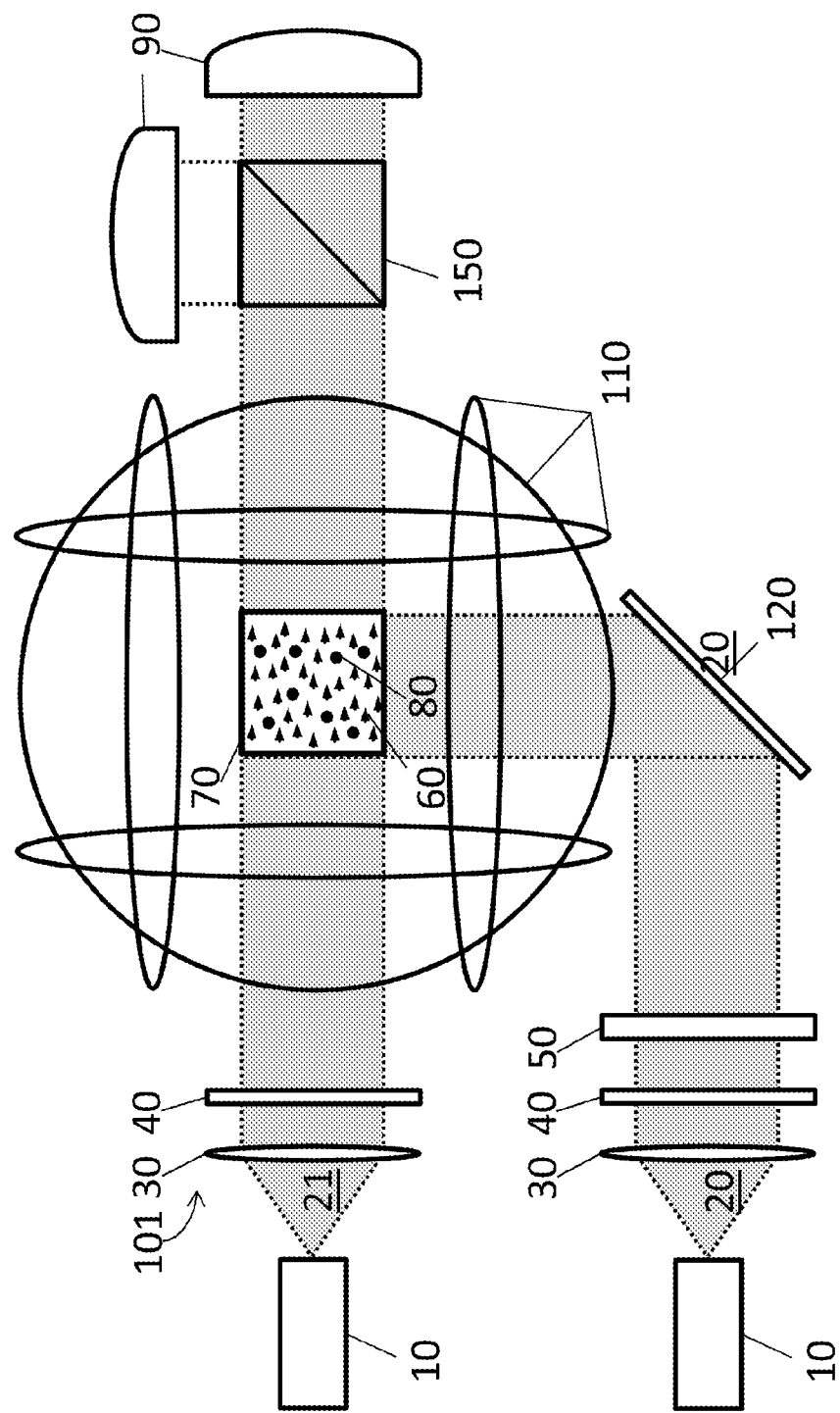
FIG. 4 schematically illustrates a prior art, perpendicular, dual beam ZF-PRM system.

The theory, construction, and operation of ZF-PRMs, whether employing a single or multiple beams, is described in prior art (Marie-Anne et al., 1971; S. J. Seltzer & Romalis, 2004; W & E, 1974). FIG. 1 schematically illustrates a single beam ZF-PRM used to measure background magnetic field. Similar components are used whether a single or multiple beams are employed, and regardless of the way the beams are configured, whether they are parallel as shown in FIG. 3, or perpendicular, as shown in FIG. 4. Additionally, the systems shown in FIGS. 1, 3, and 4 may be modified by a person skilled in the art to create the example system and perform the example method as presented by the inventors herein.

As shown in FIGS. 1, 3, and 4, a ZF-PRM apparatus 101, comprises a cell 70 containing an alkali metal vapor or helium 60. The cell 70, which can be made of glass, or some other transparent material, can also include a buffer gas 80. The buffer gas may comprise a noble gas such as helium, argon, xenon or neon. Another gas such as nitrogen can also be used as buffer gas 80. The buffer gas may comprise of a mixture of gases or a single component gas. The cell 70 may be heated to an elevated temperature to provide a density of alkali metal atoms, which can range from at least about $10^7$ cm$^{-3}$ to at least about $10^{15}$ cm$^{-3}$ or more. The exact temperature to which the cell 70 is heated will depend, in general, upon the atomic species (e.g. sodium, potassium, rubidium, or cesium) which is used in the apparatus. As an example, when the alkali metal comprises rubidium-87, the cell 70 may be heated to about room temperature or up to about 200° C. The cell 70 may be heated by locating the cell within an oven (not shown) or by placing it within thermal proximity to a heating element.

In the ZF-PRM 101, a pump light beam 20, which can be generated by a laser 10, or a vapor lamp 10, is directed through a linear polarizer 40 to linearly polarize the pump light beam 20. The linear polarizer 40 can be omitted if the pump light beam 20 is already linearly polarized. The pump light beam 20, which can have an optical power level of up to a few microWatts (μW) or more depending upon the size and temperature of the cell 70, can be expanded and substantially collimated by one or more lenses 30. The pump light beam 20 can be expanded, for example, from fraction of a millimeter (mm) to a size which fills a majority of the internal volume of the cell 70, as shown in FIG. 1. The cell may have lateral dimensions of generally about one mm or larger.

After being expanded and substantially collimated by the lenses 30, the pump light beam 20 may be directed through an optical waveplate 50 having a fast axis which is oriented at 45° with respect to a direction (e.g. vertical out of the plane of FIG. 1 or horizontal in the plane of FIG. 1) of the linear polarization of the pump light beam 20. In this way, the optical waveplate 50 converts the pump light beam 20, which was initially linearly polarized, into being circularly polarized. The circularly-polarized light in the beam 20 after passing through the optical waveplate 50 can be either right-handed circularly-polarized light or left-handed circularly-polarized light. After being transmitted through the optical waveplate 50, the pump light beam 20 is directed through the cell 70 containing the alkali metal vapor 60. For example, if two light beams, a circularly polarized pump light beam 20 and linearly polarized probe beam 21, are employed for instance in parallel fashion, as in FIG. 3, a beam splitter 150 may combine the pump light beam 20 and the probe beam 21 into a combined light beam 22 before they are directed towards the cell 70. If two beams are directed at the cell in a perpendicular fashion, as illustrate in FIG. 4, a beam 20 may be re-directed as such by a mirror 120, and presented to the vapor cell along with the probe beam 21.

The optical waveplate 50 functions as a quarter waveplate at the wavelength of the pump light beam 20, which is substantially equal to the wavelength of a first or second D1 line atomic transition of the alkali metal vapor 60. D1 line is defined herein as a transition from a $n^2S_{1/2}$ ground state to a $m^2P_{1/2}$ excited state of the alkali metal atoms in the vapor 60 where n and m are integers. The pump light beam 20 need not be exactly on line center of the D1 transition, but can be tuned off the line center and onto the wings of the D1 transition.

The buffer gas 80 (e.g. helium, neon or nitrogen) which is in the cell 70 is useful to slow down the rate at which the atoms of the alkali metal vapor 60 collide with the inner walls of the cell 70 which can again randomize the spins of the alkali metal atoms. The buffer gas 80 pressure in the cell 70 can be, for example, in a range between about 1 torr and about 2000 torr. Special coatings on the inner walls of the cell 70, such as octadecyltrichlorosilane (OTS) or paraffin, may be used in lieu of, or in addition to, buffer gases 80 to reduce spin randomization from wall collisions.

The pump beam 20, after passing through the vapor cell 70, is collected by a one or more photodetectors 90, which provide(s) a measure of the amount of light transmitted through the cell 70, or a measure of the polarization state of the light transmitted through the cell 70. Various types of photodetectors 90 may be used with detection capability in the wavelength range of the pump light beam 20. The output of the photodetector may be subsequently amplified using suitable low noise electronic controllers 100 (not shown in FIGS. 3 and 4). The beam, having passed through the vapor cell, may be split, by a beam splitter 150, and directed to multiple photodetectors 90, as shown in FIGS. 3 and 4.

The ZF-PRM apparatus 101, the cell 70 alone, or a space or room where the ZF-PRM is housed, may be surrounded by one or more, or one or more sets of electrically activated magnetic coils 110, a set of coils being three coils, one generating fields in the x-plane, one generating fields in the y-plane, and one generating fields in the z-plane, that generate magnetic fields opposing a background field, substantially cancelling out, zeroing, nulling, or optimizing the resonance of any magnetic field in the region around the cell 70. An electronics controller 100 (not shown in FIGS. 3 and 4) for the coils 110, or magnetic field component may be programmed or manually operated to modify the direction and magnitude of the magnetic field produced by the coils in order to zero or null the magnetic field therefor optimizing the ZF resonance at the location of the vapor cell 70.

When the alkali atoms 60 in the cell 70 are in a zero magnetic field environment, the circular polarization of the pump light beam 20 produced by the optical waveplate 50 aligns the nuclear and electron spins of the individual alkali metal atoms in the alkali metal vapor 70 from optical pumping process (Napper & Mathur, 1967). The optical pumping process re-orients the spins of the individual alkali metal atoms so that they are in a magnetically-polarized state aligned along the direction of the pump light beam 20 (i.e. defined here in as the z-direction, as shown in FIG. 1).

Figure 2:
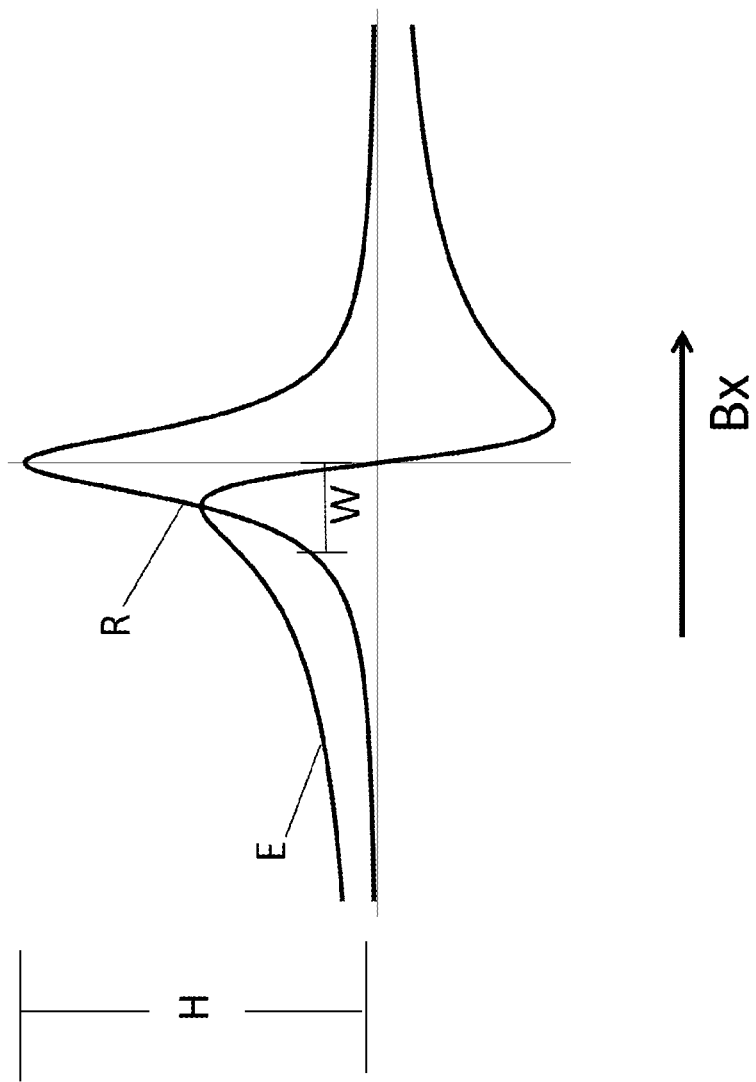
FIG. 2 illustrates a resonance peak and a dispersion peak.

The amount of pump light 20 transmitted by the vapor cell 70 and collected by the photodetector 90 is proportional to the degree of spin polarization of the alkali atoms 60 in the z-direction, Pz. The value of Pz is given by Eq. 2. When the cell 70 is in a ZF environment, i.e. Bx=By=Bz=0, scanning the magnetic field, Bx 140 for example, produces a narrow Lorentzian resonance, defined herein as the natural ZF resonance, which can be seen by monitoring the amplified output of the photodetector 90 on an oscilloscope. A resonance R, as shown in FIG. 2, is referred to in the prior art as the ZF resonance. The resonance R, or any resonance, may be defined has having a height, H, and a width W. It should be understood that modification of the ZF-PRM to include additional probe light beams, for example illustrated in FIGS. 3 and 4, may change the shape of the resonance peak but these peaks may still be defined by a height and a width.

The width W of the ZF resonance R in the x-direction is given by Eq. 3, and the height H or amplitude of the resonance is given by Eq. 4. The derivative of the resonance R is a dispersion curve, referred to herein as error signal E. It is well known in the art that an error signal E can be created by applying a modulation to a resonance R, for example by modulating a magnetic field, and then using a lock-in detector for demodulation. When By=Bz=0, the resonance has the smallest width (R/γ) and the largest amplitude $P_0$. Therefore the magnetometer is maximally sensitive when Bx=By=Bz=0.

As discussed above various algorithms and additional equipment are available for detecting the ZF resonance and directing the coils 110 to produce an environment in which Bx=By=Bz=0 at the vapor cell 70. Alternately, the present example is a system and method for simply, inexpensively, and quickly detecting the ZF resonance and setting the electrically activated magnetic field coils 110 in a way that Bx=By=Bz~0 in the neighborhood of the vapor cell 70, without the use of additional equipment or complex and time consuming algorithms.

Figure 5:
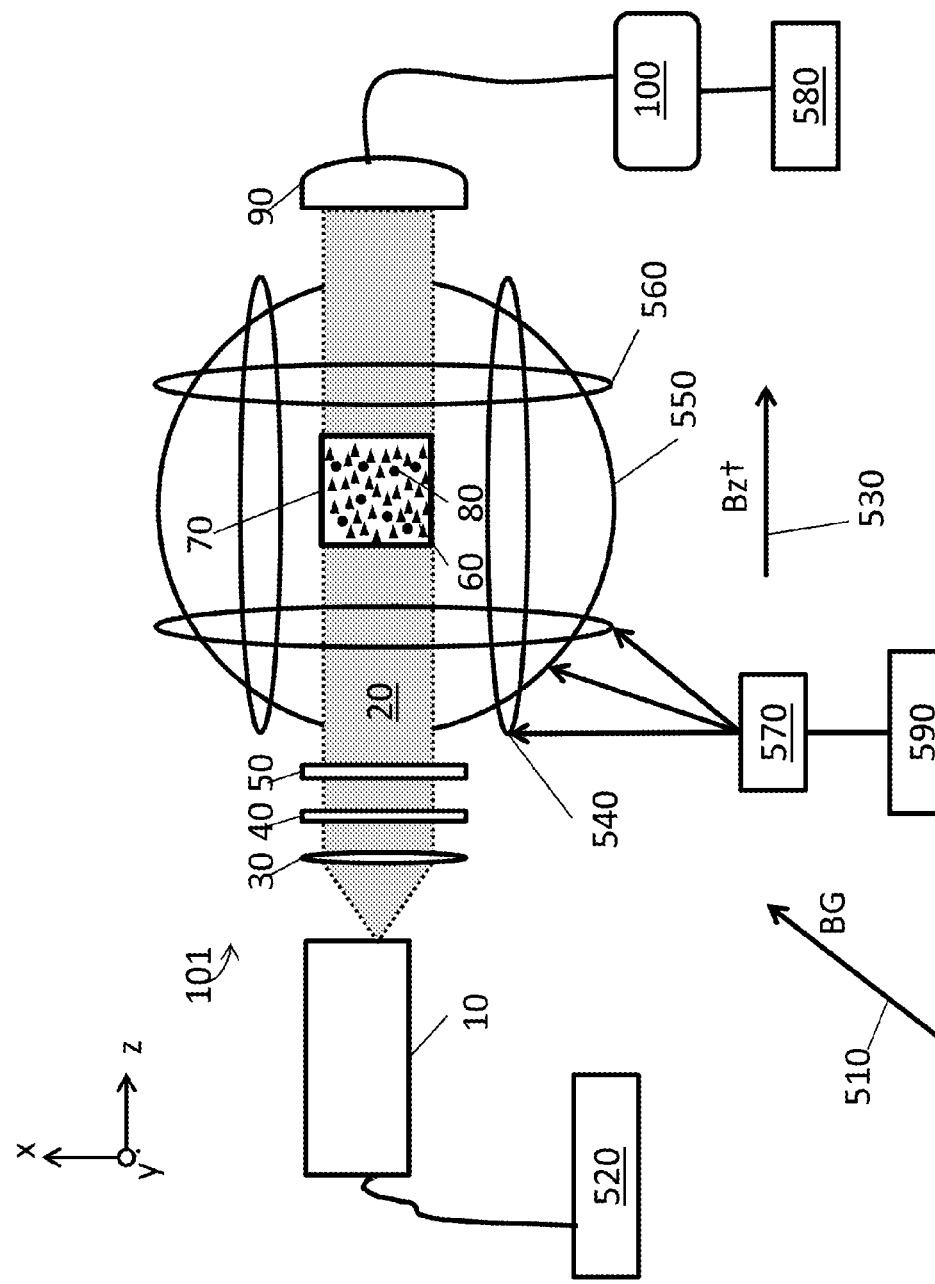
FIG. 5 schematically illustrates an example manual system for identifying and optimizing a ZF resonance.

To describe the present example system and method, FIG. 5 schematically illustrates a manual system and method for identifying and optimizing a ZF resonance. As such, a ZF-PRM 101, simply referred to as a magnetometer, may be placed in an environment with potentially non-zero background magnetic field. This ZF-PRM would necessarily encompass components described above including one or more laser or light source(s) 10, that generates a beam 20, that may pass through any number a beam splitters (not shown), polarizers 30, lenses 40, and/or waveplates 50. The beam would pass through a cell 70 containing target alkali atoms or helium 60, and optionally a buffer gas 80. One or more, or one or more sets of magnetic coils 540, 550 and 560, producing magnetic field components in the x-, y- and z-direction, respectively, would be employed to null the ambient magnetic field in the region around the cell 70. This has the effect of minimizing the width, and maximizing the height of the ZF resonance, and thereby optimizing the ZF resonance. The coils 540, 550 and 560, which may also be Hemholz coils, are electrically powered by a coil driver 570.

The magnetometer 101 may be placed in an arbitrary orientation with respect to the background magnetic field BG 510. The system employs a coil driver 570 to produce a strong magnetic field $Bz^t$ 530 along the direction of the pump beam, for example using a Helmholtz coil pair 560. The value of the $Bz^t$ 530, may preferably be at least equal to or greater than the maximum field to which the ZF-PRM is expected to be exposed, although a smaller bias or longitudinal magnetic field may also be used.

From Eq. 3, the said bias field $Bz^t$ 530 greatly increases the width of the resonance, and also maximizes the amplitude or height of the resonance. As an example, in the limiting case in which $Bz^t$ is significantly greater than Bx, By, Bz, R/γ, the width of the ZF resonance becomes about equal to $Bz^t$. In addition, the amplitude of the resonance, which is proportional to Pz, takes on its maximum value equal to $P_0$ from Eq. 4.

Figure 6:
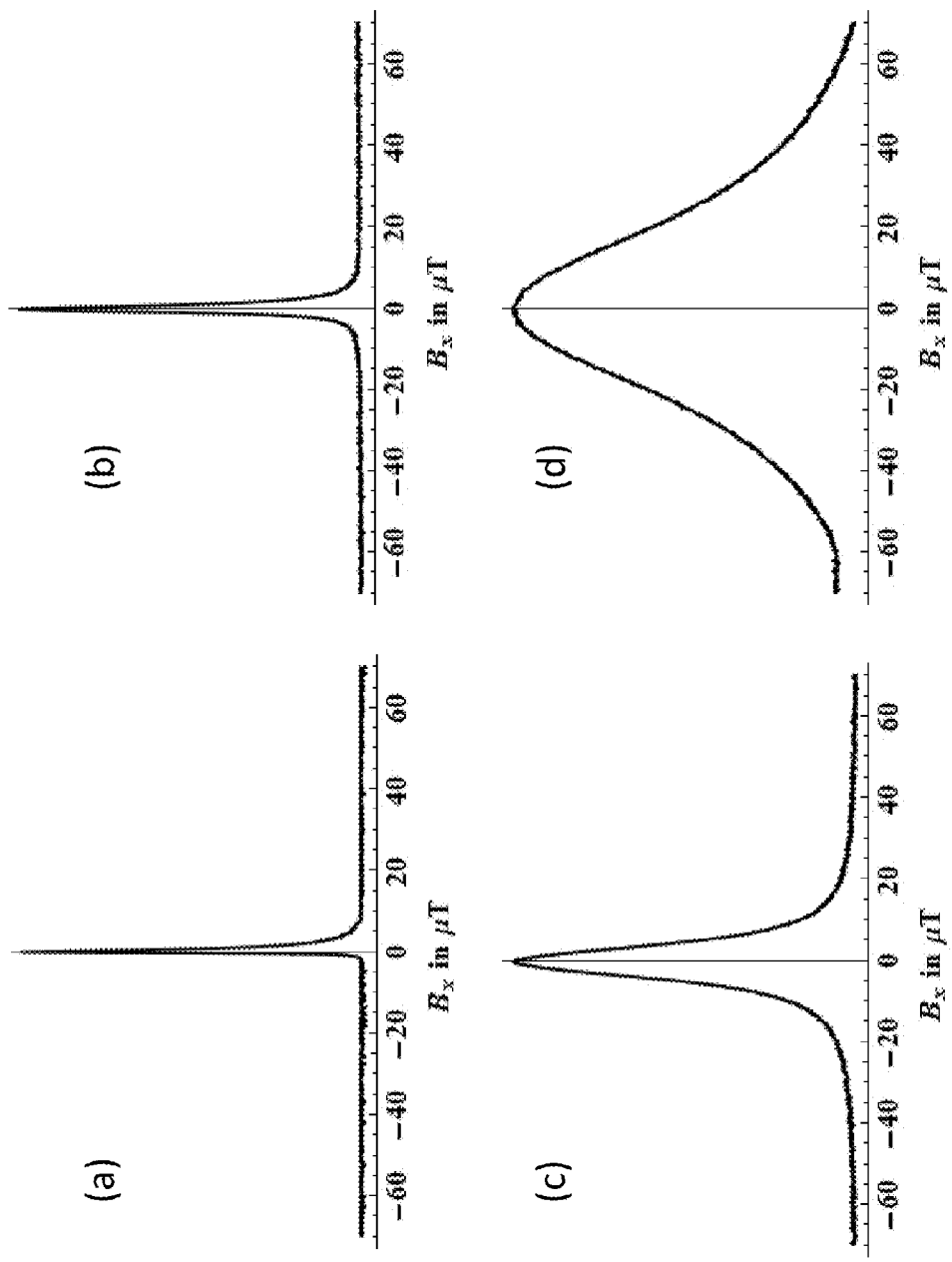
FIG. 6 illustrates a ZF resonance peak and the subsequent broadening of the resonance peak due to increasingly amplifiying a bias field $Bz^1$.

FIGS. 6(a)-(d) illustrates this change in the width of the ZF resonance as the bias field $Bz^t$ 530 is applied and amplified. FIG. 6(a) illustrates the ZF resonance in a ZF environment, prior to application of the bias field 530. FIGS. 6(b)-6(d) shows plots of the observed magnetic resonance at gradually increasing values of the bias field $Bz^t$ 530. As the bias field is amplified, the width of the ZF resonance increases, as shown in FIGS. 6(b), 6(c), and 6(d). Due to this increase in width, the ZF resonance signal may be found and identified very easily by the non-iterative application of a strong bias field $Bz^t$ 530.

Initially if the magnetometer 101 was in a non-zero magnetic field, the ZF resonance in plot FIG. 6(a) likely would not be observed, when the bias field $Bz^t$ 530 is not present. The resonance would gradually appear in subsequent plots FIGS. 6(b)-6(d), with the resonance becoming wider and stronger as the bias field $Bz^t$ 530 is applied and increased in value.

By scanning the magnetic field in a direction differing from that of the pump beam or bias field $Bz^t$, either being in the x-direction or in the y-direction, or any other direction which may be, for example, substantially perpendicular to the pump beam 20, for example using Helmholtz coils 550 or 540, the ZF resonance can be observed on an oscilloscope 580 by monitoring the photodetector 90 output of the magnetometer 101, after amplification using suitable low noise electronics 100. The scan range of the said differing or substantially perpendicular field may be in the range of 0.1 times, to about 10 times as strong as the bias field $Bz^t$. Preferably, the scan range may be as large as the magnitude of the bias field or greater. The signal for scanning the magnetic field may be applied using a signal generator 590 controlling the output of the coil driver. The scan rate may be a set at a value, preferably between 0 Hz and 1 kHz.

Figure 7:
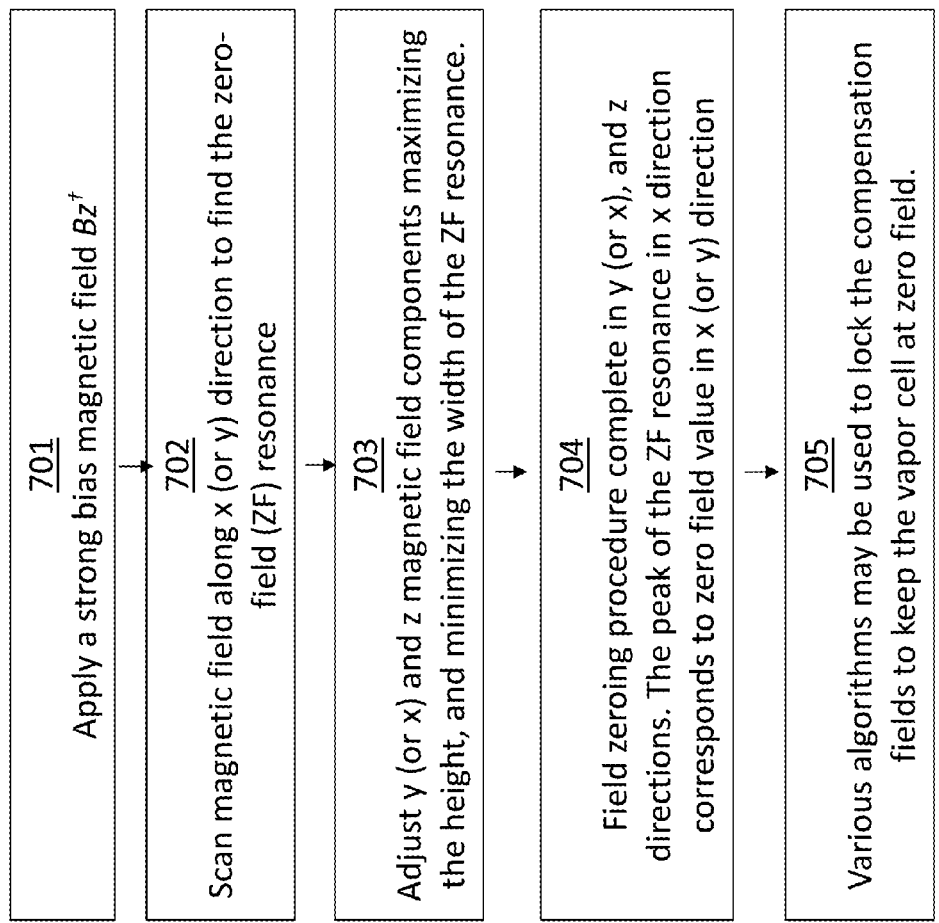
FIG. 7 illustrates a flow sheet for the method for optimizing the ZF resonance by manually adjusting magnetic field components.

FIG. 7 illustrates a flow sheet for the method of identifying and optimizing a ZF resonance for the system presented in FIG. 5. In ZF-PRM system, wherein a pump beam is directed through a vapor cell containing gaseous atoms, a first step, a strong magnetic field $Bz^t$ 530 is applied 701. This is accomplished by control of the 560 coils in the z-direction. After the bias field is applied, the magnetic field is scanned in a direction different from that of the pump beam which may be substantially perpendicular to the pump beam 20, referred to herein as the x-direction, to find the ZF resonance 702. Once the ZF resonance is identified on the oscilloscope 570, the next step 703 is to adjust the magnetic field components in the y- and z-directions by adjusting the current flowing through the Helmholtz coils 550 and 560 respectively. While observing the resonance, on an oscilloscope for example, the magnetic field values in the y- and z-direction can be adjusted by changing the outputs from the coil driver 570 in a way that minimizes the width of the resonance and maximizes its amplitude.

The coil driver 570 settings at which the sharpest resonance (minimum width and maximum amplitude) is observed corresponds with magnetic field being closest to zero in the y- and z-directions at the location of the vapor cell 70 in the magnetometer 101. The peak of the ZF resonance corresponds with the magnetic field value closest to zero in the x-direction at the location of the vapor cell 70 in the magnetometer 101.

This completes the procedure 704 for initially zeroing of the magnetic field at the location of the vapor cell 70, readying the ZF-PRM for operation to measure external magnetic fields. To measure a field of interest, various prior art algorithms can be used 705 to operate the magnetometer 101, and/or to keep the magnetometer 101 locked at the ZF value.

Figure 8:
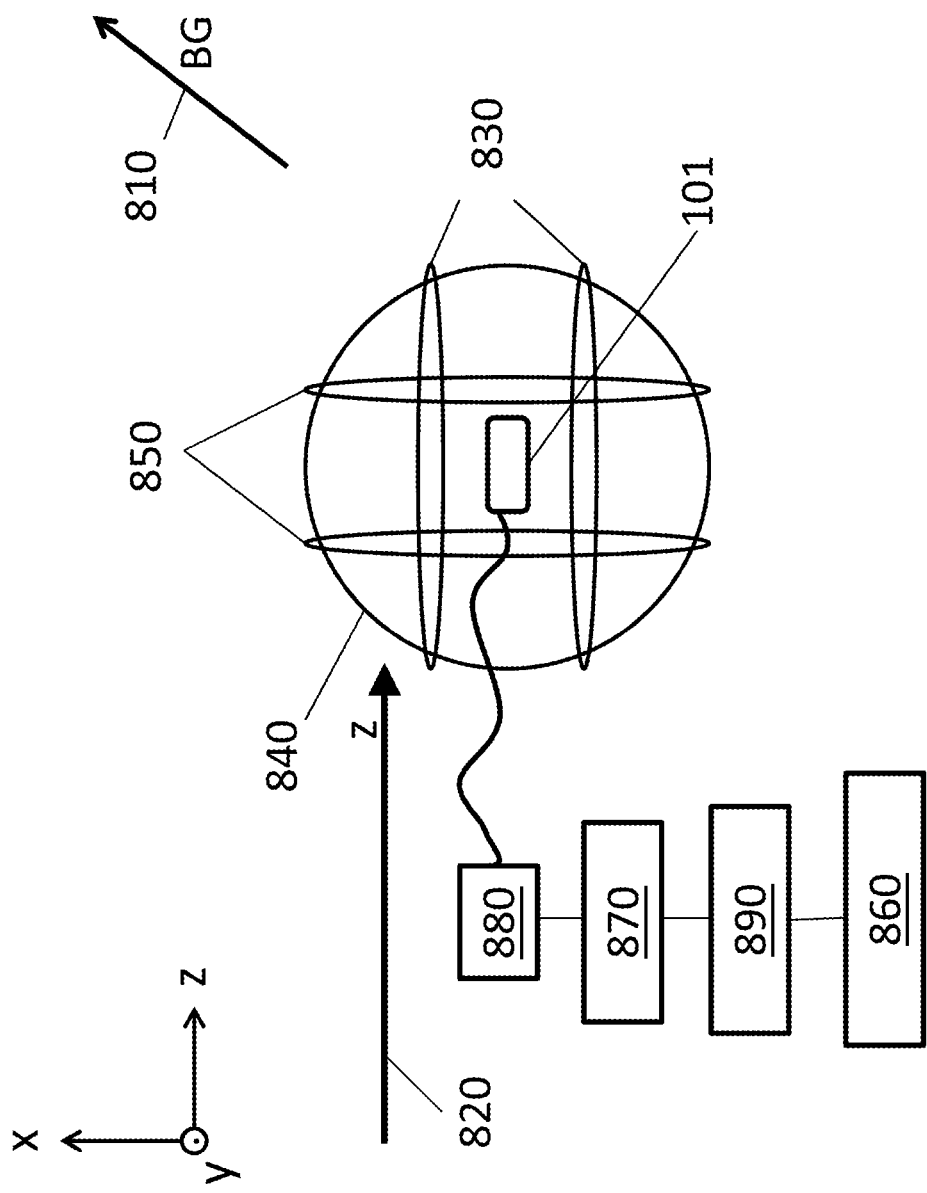
FIG. 8 schematically illustrates an example electronic system for locking a ZF resonance.

An example electronic system and method for locking a ZF-PRM to a ZF resonance is schematically illustrated in FIG. 8. The magnetometer 101 described in FIG. 1 is placed in a non-zero magnetic field, for example outside, such that it may be exposed to the earth's magnetic field in a magnetically unshielded environment as shown in FIG. 8. The magnetometer 101 may be placed in an arbitrary orientation with respect to the background magnetic field BG 810. As in the manual method, a strong magnetic bias field 820 is applied using Helmholtz coil pair 850 in the direction of the pump beam 20 (see FIG. 5), referred to herein as the z-direction. The longitudinal bias field 820 may be stronger than the maximum field BG 810 the magnetometer 101 is expected to experience, and preferably twice as strong. The Helmholtz coils are electrically powered by a coil driver 860.

At least one or up to three separate sinusoidal magnetic field modulations, or modulation currents, may be applied to the magnetometer 101 in the x-, y-, and z directions using Helmholtz coils 830, 840, and 850 respectively. The electronic modulation signals may be generated by three separate lock-in amplifiers 870, or separate and/or additional amplifiers, and applied using a coil driver 860, which powers the Helmholtz coils 830, 840, and 850. The amplitude of the modulation current is adjusted such that the peak-to-peak value of the oscillatory magnetic field produced by each coil pair 830, 840, and 850 at the location of the vapor cell is about 50 nT or greater.

The sinusoidal modulation applied to each of the coils is at a different frequency, preferably in a range between 50 Hz and 5 kHz. In an advantageous embodiment, the frequency of the modulation in the x- and the y-direction is the same, but differs in phase, substantially equal to π/2 radians. The modulation in the z-direction is at a different frequency.

The magnetic field modulation generated by the coils, 830, 840, and 850 causes the alkali spins in the magnetometer to oscillate, which in turn, modulates the intensity of the pump beam measured by the photodetector 70 in the magnetometer 101. The photodetector output is amplified using a photodiode amplifier 880. The amplified photodetector signal is subsequently fed to the lock-in amplifier 870.

Each of the three lock-in, separate, or additional amplifiers 870 receive(s) the same input signal from the photodetector amplifier. However, the reference signal for demodulation for the x-axis channel of the lock-in amplifier is the modulation signal applied to the x-axis coil 830, the reference signal for demodulation for the y-axis channel of the lock-in amplifier is the modulation signal applied to the y-axis coil 840, and the reference signal for demodulation for the z-axis channel of the lock-in amplifier is the modulation signal applied to the z-axis coil 850. In this way, each of the three lock-in amplifier generates an independent, demodulated output signal proportional to the magnetic field in each of the three, x-, y-, and z-directions. The demodulation phase for lock-in amplifier in each case is adjusted in a way that generates the strongest error signal. The maximum filter time-constant is preferably adjusted to be roughly equal to the inverse of the relaxation rate of alkali spins.

After the bias field is applied, the output from at least one of the lock-in amplifier channels is fed to a control loop 890, that may in a non-limiting example be a proportional-integral-differential (PID) box, which generates feedback signals with appropriate time constants and polarity for locking over the ZF resonance. If more than one amplifier channel is used each may be fed to a separate control loop.

The output from the control loop 890 is fed to the coil drivers for the three coils 830, 840, and 850. The feedback loops for the x coils 830 and the y coils 840 are preferably engaged prior to engaging the feedback for the z coils 850. Once all the control loops are engaged, the magnetic field generated by the coils 830, 840 and 850 self-converge in a way that produces a zero magnetic field environment at the location of the vapor cell in the magnetometer.

Because the ZF resonance is significantly broadened by the bias field 820, which is stronger than the ambient field, the resonance is always within the capture range of all three control loops. This is one of the significant benefits of our approach, which eliminates the need for complex algorithms for finding and locking over the ZF resonance.

The background magnetic field is measured from the input current of the coils 830, 840 and 850 once all the feedback loops converge over the zero-field resonance. The current-to-field conversion may be mathematically calculated based on geometry of the coils, or pre-calibrated in a laboratory.

Figure 9:
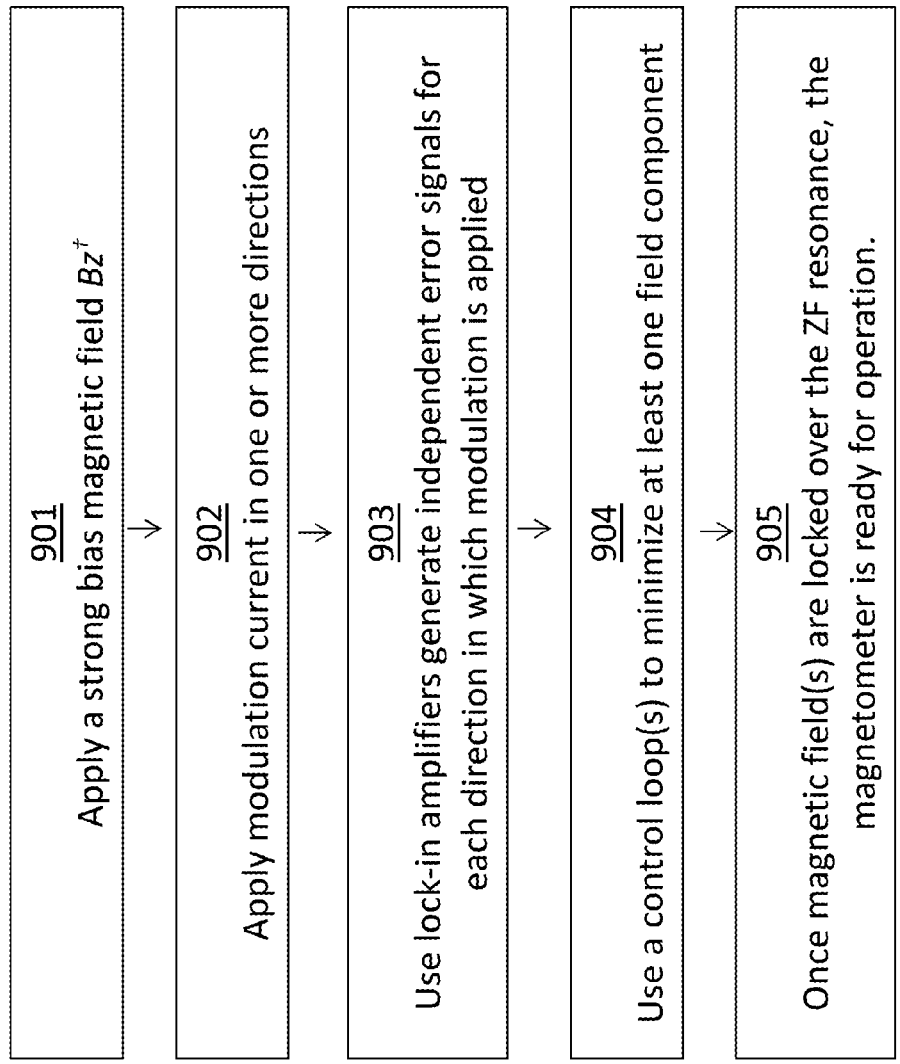
FIG. 9 illustrates a flow sheet for the method for electronically optimizing the ZF resonance by applying a modulation current and engaging a control loop to optimize a field component.

FIG. 9 illustrates a flow sheet for the method of electronically locking a ZF resonance. This flow sheet illustrates the main steps described below. In a ZF-PRM system wherein a light beam is directed at a vapor cell containing gaseous atoms, a strong magnetic bias field $Bz^t$ is applied 901. In addition to the bias field, at least on magnetic field modulation is applied in one of the three orthogonal directions 902 using external coils (FIG. 8, 830, 840 and/or 850). The magnetic modulation for example may be a sinusoidal, square, or any other periodic oscillatory function. The frequency of the modulation field can be in at least 10 Hz, or at least 20, or at least 50 Hz, or even at least 100 kHz. The amplitude of the modulation preferably may be chosen in a way that generates an error signal with the steepest slope in a ZF environment, although other modulation amplitude settings are also possible, including dynamic updating of the modulation amplitude. The modulation along each of the three axes may be the same, or differ in frequency or phase. If the modulation differs in frequency or phase this may allow generation of independent outputs for each direction.

Using the modulated output from the photodetector 90 (FIG. 5), lock-in detection techniques described in prior art can be used to generate three separate error signals corresponding to each of the three orthogonal axes 903 (H. f. Dong, Fang, Zhou, Tang, & Qin, 2012). All the lock-in amplifiers may be simultaneously active, or may be sequentially activated one after another in no specific order. For a bias field $Bz^t$ greater than around twice the magnitude of the background field, the resonance is always within the linear region of the error signal.

Next, using a control feedback loop, the signal lock can be engaged to drive the magnetic field values to the ZF value in all three directions 904. The feedback loops for the x-coils 830 and the y coils 840 are preferably engaged prior to engaging the feedback for the z-coils 850. Once all the control loops are engaged, the magnetic field generated by the coils 830, 840 and 850 self-converge in a way that produces a zero magnetic field environment at the location of the vapor cell in the magnetometer. Once all feedback loops converge, the feedback loops may be disengaged, or they may remain engaged based on desired operation mode of the ZF-PRM, for example, to measure a sample field.

Once the background field is zeroed, a precision field environment can be created by disengaging the feedback loop and adding a field generated by a calibrated coil. A calibrated coil is one which has been measured and verified to produce a known field for a given drive current or voltage. Further a precision field environment can be created by leaving the feedback control loop engaged and simply adding a calibrated offset to the feedback control loop. A calibrated offset is a signal with a value that, when added to the error signal, produces a known field.

There are many different procedures and steps that a person skilled in the art can use to find the ZF resonance using the invention disclosed here, and the steps described here are just one example. It is understood that the exact operational details may differ based on the implementation and configuration of the ZF magnetometer, but the basic premise of employing a bias field in the direction of the pump beam to increase the width and the amplitude of the ZF resonance peak allowing quicker detection of ZF resonance remains applicable to all configurations. As an example, in a perpendicular pump-probe ZF-PRM (Romalis, Kornack, Allred, Lyman, & Kominis, n.d.), the ZF resonance shape is a dispersive Lorenztian instead of the symmetric Lorenztian resonance R in FIG. 2 observed using ZF-PRM described in FIG. 1. Thus while the specific implementation of feedback loops and control electronics may differ, the benefits of providing a longitudinal bias field in the same direction as the pump light source remain equally applicable.

While various embodiments have been described in detail, it is apparent that modifications and adaptations of those embodiments will occur to those skilled in the art. However, is to be expressly understood that such modifications and adaptations are within the spirit and scope of the present disclosure.

EXAMPLES

Example 1

A ZF-PRM, simply referred to here as a magnetometer, was constructed in the following manner. The magnetometer housed a glass vapor cell in a shape approximating a cube having dimensions of about 4 mm)×4 mm×4 mm. The cell was vacuum processed and filled with an alkali vapor consisting of enriched rubidium-87 at a purity level exceeding 80% compared to other rubidium isotopes. Additionally, a buffer gas was added to the cell and the cell was sealed by melting the glass fill stem. The cell was mounted into a custom-built, non-metallic housing. A fiber coupled diode laser at about 795 nm was used to create a pump light beam. The diode laser was placed about 2 meters away from the magnetometer and the pump beam was delivered to the magnetometer with a polarization-maintaining, single-mode optical fiber. A lens in the magnetometer housing was used to collimate the pump beam from the optical fiber. Additional optical components such as polarizers, waveplates, and mirrors were used within the magnetometer housing to condition the pump beam and direct it through the vapor cell. A photodiode placed after the vapor cell was used to collect the transmitted pump beam. To increase the density of alkali atoms, the cell was heated to a temperature over 100° C. All components in the magnetometer housing were chosen to be either non-magnetic or to have very low residual magnetization.

We first operated the magnetometer indoors, and within a three-layer magnetic shield, to verify that the magnetometer was functioning properly. A set of three-axis Helmholtz coils were positioned inside the magnetic shield in such a way as to surround the magnetometer housing. By modulating the current in the coil assembly, a narrow ZF resonance with width of about 30 nT was observed. Because of the magnetic shields and the ZF conditions inside the shields, we were able to immediately find the resonance without having to search for it. Three independent control loops were set up using lock-in amplifiers which applied feedback to the three-axis coils. Using this setup, we were able to lock the field to the peak of the ZF resonance in all three directions. The modulation frequencies for the transverse directions (perpendicular to the pump beam) were at the same frequency, but differed in phase by pi/2 (90 degrees). The modulation depth was about 50 nT at the location of the vapor cell. With this setup we were able to reach sensitivities of about 5 fT/sqrt (Hz).

Example 2

The magnetometer described above was placed in a non-shielded, open-air environment, randomly oriented with respect to the Earth's magnetic field. Using the iterative prior art method of stepping through the bias field, we characterized the time required to find the zero-field resonance of a ZF-PRM magnetometer in this un-shielded environment. The magnetometer was oriented so that Earth's field was not substantially along the direction of the pump beam. We turned on the pump beam and did not observe a ZF resonance due to the unknown field and direction. We started our search for the ZF resonance by setting the applied z-bias field to zero and stepping through values of x-bias fields and y-bias fields. After searching through values of x-bias fields and y-bias fields, we reset the x and y values and made a small change in the z-bias field. We then began our search anew by adjusting x-bias fields and y-bias fields for that particular z value. We iterated this process for over an hour and were not able to find the resonance.

Example 3

To test the efficiency and ease of use of the example magnetometer system and method of the present invention, the magnetometer, described above, was again located in an un-shielded, open air environment exposed to the Earth's magnetic field as in Example 2. As in Example 2, we oriented the magnetometer so that Earth's field was not substantially along the direction of the pump beam. We turned on the pump beam and did not observe a ZF resonance due to the unknown field and direction. Using the z-bias coils we applied a magnetic bias field, $Bz^t$, , in the direction of the pump beam which is along the z-axis. The applied field had a magnitude of about 100 µT which is about twice Earth's magnetic field, or in other words about twice the maximum expected field. Immediately after applying the bias field $Bz^t$, a strong transmission signal was easily observed due to the induced broadening of the resonance and the increased strength of the resonance. By scanning the current in the coil assembly, we observed a broad ZF resonance with width of about 100 µT. Because of the broadening of the ZF resonance, we were able to immediately find the resonance without having to search for it. We initialized three independent control loops using lock-in amplifiers which applied feedback to the three-axis coils. The control loops for the x- and y-bias fields were engaged first and the field was zeroed in these two directions. After that, the control loop for the z-direction was engaged which forced the z-field to zero. Using this example system, we were able to lock the field to the peak of the ZF resonance in all three directions. The modulation frequencies for the transverse directions (x- and y-directions) which are perpendicular to the pump beam were at the same frequency, about 500 Hz, but differed in phase by pi/2 (90 degrees). The modulation frequency of the z-bias was at about 850 Hz. The modulation depth was about 50 nT, or greater, at the location of the vapor cell. With this example system and method, we were able to find the ZF resonance in less than about one second which was the time to manually engage the PID control loop for the z-bias field. This time can be shortened to about several milliseconds or less using digital control.

The example system and method described herein comprising using a magnetic coil to apply a strong bias field, $Bz^t$, along the direction of the pump light beam, allows near instantaneous identification of the ZF resonance. Once the resonance is identified, nulling fields can be immediately applied to initialize, or compensate for the ambient fields and zero, the magnetometer. Using this invention, the initialization procedure can be completed in a matter of seconds, without any need for external aids or complex and time-consuming convergence algorithms. In contrast, after over an hour's time using the iterative prior art method of stepping through the bias field incrementally, a ZF resonance could not be found. The ability to quickly initialize the magnetometer by zeroing the magnetic field in its vicinity greatly increases its practical utility of the example magnetometer.

It should be noted that the examples described above are provided for purposes of illustration, and are not intended to be limiting. Other devices and/or device configurations may be utilized to carry out the operations described herein. It can be envisioned that technology advances in the field may lead to variations of a magnetometer that may not be known at this time. The method of providing a longitudinal field in the same direction as the light source to increase the width of the detection bandwidth and therefore more easily and quickly compensate for and nullify the ambient magnetic field, however, will still be applicable to such systems.

REFERENCES

Budker, D., & Romalis, M. (2007). Optical magnetometry. *Nat Phys*, 3(4), 227-234. doi:10.1038/nphys566

Dong, H. f., Fang, J. c., Zhou, B. q., Tang, X. b., & Qin, J. (2012). Three-dimensional atomic magnetometry. *The European Physical Journal—Applied Physics,* 57(02), null-null. doi:10.1051/epjap/2011110392

Dong, H., Lin, H., & Tang, X. (2013). Atomic-Signal-Based Zero-Field Finding Technique for Unshielded Atomic Vector Magnetometer. *IEEE Sensors Journal,* 13(1), 186-189. doi:10.1109/JSEN.2012.2216951

Dupont-Roc, J., Haroche, S., & Cohen-Tannoudji, C. (1969). Detection of very weak magnetic fields (10-9 gauss) by 87Rb zero-field level crossing resonances. *Physics Letters A,* 28(9), 638-639. doi:10.1016/0375-9601(69)90480-0

Fang, J., & Qin, J. (2012). In situ triaxial magnetic field compensation for the spin-exchange-relaxation-free atomic magnetometer. *The Review of Scientific Instruments,* 83(10), 103104. doi:10.1063/1.4756046

Happer, W., & Mathur, B. S. (1967). Effective Operator Formalism in Optical Pumping. *Physical Review,* 163(1), 12. doi:10.1103/PhysRev.163.12

Marie-Anne, B., Jean, B., N, C.-T. C., A, D.-R. J., Serge, H., H, K. A., & Jean-Claude, L. (1971, Dec. 21). Paramagnetic resonance and optical pumping magnetometer in the near zero magnetic field-range. Retrieved from http://www-.google.com/patents/US3629697

Romalis, M., Kornack, T., Allred, J., Lyman, R., & Kominis, I. (n.d.). High sensitivity atomic magnetometer and methods for using same. Retrieved from http://www.google.com/patents?id=_2GTAAAAEBAJ&printsec=frontcover&dq=romalis&hl=en&ei=MzbXTpy6CuXm0QHHmtzQDQ&sa=X&oi=book_result&ct=result&resnum=1&ved=0CDIQ6AEwAA Seltzer, S. (2008). *Developments in Alkali-Metal Atomic Magnetometry* (PhD Dissertation). Princeton University.

Seltzer, S. J., & Romalis, M. V. (2004). Unshielded three-axis vector operation of a spin-exchange-relaxation-free atomic magnetometer. *Applied Physics Letters,* 85(20), 4804-4806. doi:doi:10.1063/1.1814434

Shah, V., Knappe, S., Schwindt, P. D. D., & Kitching, J. (2007). Subpicotesla atomic magnetometry with a microfabricated vapour cell. *Nat Photon,* 1(11), 649-652. doi: 10.1038/nphoton.2007.201

Slocum, R. E., & Reilly, F. N. (1963). Low Field Helium Magnetometer for Space Applications. *IEEE Transactions on Nuclear Science,* 10(1), 165-171. doi:10.1109/TNS.1963.4323257

Weinstock, H. (1996). *SQUID Sensors: Fundamentals, Fabrication and Applications* (*NATO Science Series E*: (1st ed.). Springer.

W, F., & E, O. (1974, Jan. 15). Miniature optically pumped magnetometer probe using light pipes to transmit light to the probe. Retrieved from http://www.google.com/patents/US3786340

We claim:

1. A method for identifying and optimizing a ZF resonance using a paramagnetic resonance magnetometer, the method comprising the steps of:
    a. directing at least one pump light beam through a vapor cell containing gaseous atoms to increase the magnetic polarization of the gaseous atoms;
    b. measuring light transmitted through the vapor cell;
    c. in a non-iterative action, applying a strong magnetic field having a direction along the pump light beam to simultaneously increase the height and width of the ZF resonance;
    d. subsequent to step c, detecting the ZF resonance;
    e. scanning a magnetic field in a direction differing from that of the pump light beam; and
    f. adjusting magnetic field components generated by one or more coils to minimize the width and maximize the height of the zero-field resonance.

2. The method of claim 1, wherein the magnetometer is oriented along any arbitrary direction with respect to a background magnetic field.

3. The method of claim 1, wherein the magnetometer is not placed within a magnetic shield.

4. The method of claim 1, wherein the strong magnetic field applied along the direction of the pump light beam is at least about as strong as a background magnetic field.

5. The method of claim 1, wherein the strong magnetic field applied along the direction of the pump light beam is stronger than a background magnetic field.

6. The method of claim 1, wherein the strong magnetic field applied along the direction of the pump light beam is weaker than a background magnetic field.

7. The method of claim 1, wherein the gaseous atoms in the vapor cell are selected from a group consisting of rubidium, cesium, potassium, sodium, and helium.

8. The method of claim 1, wherein scanning of the magnetic field in a direction differing from that of the pump light beam, occurs within a scan range, the scan range being from at least about 0.1 times as strong as the magnetic field applied along the pump light beam, to about 10 times as strong as the magnetic field applied along the pump light beam.

9. The method of claim 1, further enhanced for precision offset field generation, further comprising the step of adding a calibrated field.

10. The method of claim 9, wherein the calibrated field is generated by one or more coils selected from a group consisting of coils that are internal to the magnetometer and coils that are external to the magnetometer.

11. A method for locking a zero-field paramagnetic resonance magnetometer (ZF-PRM) to a ZF resonance, the method comprising the steps of:
    a. directing at least one pump light beam through a vapor cell containing gaseous atoms to increase the magnetic polarization of the gaseous atoms;
    b. measuring light transmitted through the vapor cell;
    c. in a non-iterative action, applying a strong magnetic field having a direction along the pump light beam to simultaneously increase the height and width of the ZF resonance;
    d. applying a modulation current having an amplitude to at least one coil transverse to the pump light beam;
    e. generating at least one error signal; and
    f. subsequent to step c, engaging at least one control loop to minimize at least one field component that is transverse to the pump light beam.

12. The method of claim 11, wherein the magnetometer is oriented along any arbitrary direction with respect to a background magnetic field.

13. The method of claim 11, wherein the magnetometer is not placed within a magnetic shield.

14. The method of claim 11, wherein the strong magnetic field applied along the direction of the pump light beam is at least about as strong as the background magnetic field.

15. The method of claim 11, wherein the strong magnetic field applied along the direction of the pump light beam is stronger than the background magnetic field.

16. The method of claim 11, wherein the strong magnetic field applied along the direction of the pump light beam is weaker than the background magnetic field.

17. The method of claim 11, wherein the gaseous atoms in the vapor cell are selected from a group consisting of rubidium, cesium, potassium, sodium, and helium.

18. The method of claim 11, wherein the modulation current is applied to at least two coils transverse to the pump light beam, such that at least two error signals are generated.

19. The method of claim 11, wherein the modulation current is applied to at least three coils transverse to the pump light beam, such that at least three error signals are generated.

20. The method of claim 11, further comprising the steps of:
   a. changing the amplitude of at least one modulation current; and
   b. optimizing at least one error signal.

21. The method of claim 11, further comprising the step of engaging at least one control loop that minimizes the field component in the direction along the pump beam, this step being subsequent to the step of engaging at least one control loop to minimize at least one field component that is transverse to the pump light beam.

22. The method of claim 11, further enhanced for precision offset field generation, further comprising the steps of:
   a. deactivating one or more control loops; and
   b. subsequently adding a calibrated field.

23. The method of claim 22, wherein the calibrated field is generated by one or more coils selected from a group consisting of coils that are internal to the magnetometer and coils that are external to the magnetometer.

24. The method of claim 11, further enhanced for precision offset field generation, further comprising the step of adding one or more calibrated offsets to one or more control loops.

* * * * *